United States Patent
Carlsson

[19]

[11] Patent Number: 5,851,202
[45] Date of Patent: Dec. 22, 1998

[54] DRIP CHAMBER HEAD

[75] Inventor: Per-Olov Carlsson, Sosdala, Sweden

[73] Assignee: Gambro AB, Sweden

[21] Appl. No.: 750,927

[22] PCT Filed: Jun. 28, 1995

[86] PCT No.: PCT/SE95/00797

§ 371 Date: Mar. 31, 1997

§ 102(e) Date: Mar. 31, 1997

[87] PCT Pub. No.: WO96/04944

PCT Pub. Date: Feb. 22, 1996

[30] Foreign Application Priority Data

Aug. 15, 1994 [SE] Sweden ................................. 9402721

[51] Int. Cl.⁶ ................................................. A61M 5/00
[52] U.S. Cl. ........................................ 604/247; 604/251
[58] Field of Search .................................... 604/247, 251, 604/252, 253, 254, 255, 65

[56] References Cited

U.S. PATENT DOCUMENTS

| | | | |
|---|---|---|---|
| 4,586,925 | 5/1986 | Carlsson et al. ...................... | 604/251 |
| 4,838,865 | 6/1989 | Flank et al. . | |
| 5,098,407 | 3/1992 | Okamura ............................ | 604/252 X |
| 5,364,371 | 11/1994 | Kamen .................................. | 604/251 |

FOREIGN PATENT DOCUMENTS

| | | |
|---|---|---|
| 0 062 913 | 10/1982 | European Pat. Off. . |
| 0 106 026 | 6/1990 | European Pat. Off. . |
| 0 614 675 A1 | 9/1994 | European Pat. Off. . |
| 32 02 582 C2 | 10/1986 | Germany . |

*Primary Examiner*—Ronald Stright
*Assistant Examiner*—N. Kent Gring
*Attorney, Agent, or Firm*—Lerner, David, Littenberg, Krumholz & Mentlik

[57] ABSTRACT

Drip chamber heads are disclosed for attachment to drip chambers in which the drip chamber head includes a vertical body, a first connector for connecting the body to a blood supply, and a drip tube disposed within the body including a depending lower portion, the upper portion of the drip tube being in communication with the first connector so that blood may be supplied to the drip chamber through the first connector and the drip tube, thereby providing the blood at an adjustable level within the drip chamber with an air filled region thereabove, a second connector disposed at the upper portion of the body for communicating with the air filled region of the drip chamber, and an air permeable filter disposed at the upper portion of the body between the second connector and the adjustable level of blood within the drip chamber whereby the air pressure within the air filter region of the drip chamber can be sensed through the second connector.

11 Claims, 2 Drawing Sheets

DRIP CHAMBER HEAD

FIELD OF THE INVENTION

The present invention relates to a drip chamber head intended to be attached to the upper region of a vertically arranged drip chamber.

BACKGROUND OF THE INVENTION

Drip chambers are known to be used in an extracorporeal blood circuit as an air separator to ensure that air does not accompany the blood as it is returned to a patient connected thereto.

The drip chamber is integrated in a set of tubes for use in dialysis, such as hemodialysis, hemodiafiltration or hemofiltration. The set of tubes cooperates with a dialysis machine comprising pumps and other equipment for performing and monitoring the dialysis process. Such pumps can be of the peristaltic type, which act on the exterior of a portion of a tube and force the blood within the tube along the tube.

An example of a drip chamber and its integration in a set of tubes and cooperation with a dialysis machine is described in European Patent No. 106 026, particularly FIG. 1 thereof. How a drip chamber can be designed is described in European Patent No. 614 675.

A drip chamber consists of a tube having considerably greater cross-section than corresponding connected blood tubes. The blood in the drip chamber thus provides a reduced flow velocity, which results in separation of any air bubbles in the blood. At its upper end, the drip chamber is provided with a head having several inlets with various functions, as described in greater detail in European Patent No. 106 026.

SUMMARY OF THE INVENTION

The object of the present invention is to improve upon the type of drip chamber head described in European Patent No. 106 026, and to provide a drip chamber head in which the tube arrangement is further simplified compared to the previously known drip chamber head.

In accordance with the present invention, these and other objects have now been accomplished by the invention of a drip chamber head for attachment to a drip chamber in which the drip chamber head comprises a vertically arranged body portion having an upper portion and a lower portion and including first connection means for connecting the body portion to a supply of blood and a drip member disposed within the body portion and including an upper portion and a depending lower portion, the upper portion of the drip member in communication with the first connecting means whereby the blood may be supplied to the drip chamber through the first connecting means and the drip member, thereby providing the blood at an adjustable level within the drip chamber with an air filled region thereabove, second connecting means disposed at the upper portion of the body portion communicating with the air filled region of the drip member, and an air permeable filter disposed at the upper portion of the body portion between the second connecting means and the adjustable level of the blood within the drip chamber whereby the air pressure within the air filled region of the drip chamber can be sensed through the second connecting means.

In accordance with one embodiment of the drip chamber head of the present invention, the body portion includes a lower body portion and an upper body portion comprising a cap for closing off the lower body portion, the filter being arranged between the lower body portion and the cap. Preferably, the cap includes the second connecting means. In a preferred embodiment, the second connecting means comprises a transversely extending nipple.

In accordance with another embodiment of the drip chamber head of the present invention, the filter comprises a membrane, preferably a membrane having a pore size of about 0.2 $\mu$m.

In accordance with another embodiment of the drip chamber head of the present invention, the drip chamber head includes rib means extending transversely across the upper portion of the body portion thereby forming air passage means between the second connecting means and the air filled region of the drip chamber. Preferably, the rib means comprises a plurality of rib members.

In accordance with another embodiment of the drip chamber head of the present invention, the drip chamber head includes rib means extending transversely across the upper portion of the lower body portion thereby forming passage means between the second connecting means and the air filled region of the drip chamber, the rib means providing support for the filter. Preferably, the rib means comprises a plurality of rib members. In a preferred embodiment, the rib means comprises first rib means, and the drip chamber head includes second rib means disposed in the cap above the filter for providing further support for the filter.

One particular object of the present invention is to integrate a blood filter into the drip chamber head for connection to a pressure sensor in a dialysis machine. The blood filter is thus provided with a fixed connection nipple which cooperates directly with a pressure sensor connection on the front of the dialysis machine, as described in greater detail in the simultaneously filed co-pending International Application No. . . . (corresponding to Swedish patent application Ser. No. 94.02720-8).

BRIEF DESCRIPTION OF THE DRAWINGS

The invention will be described in greater detail below with reference to the embodiments of the invention shown in the drawings.

DETAILED DESCRIPTION

Figure 1:
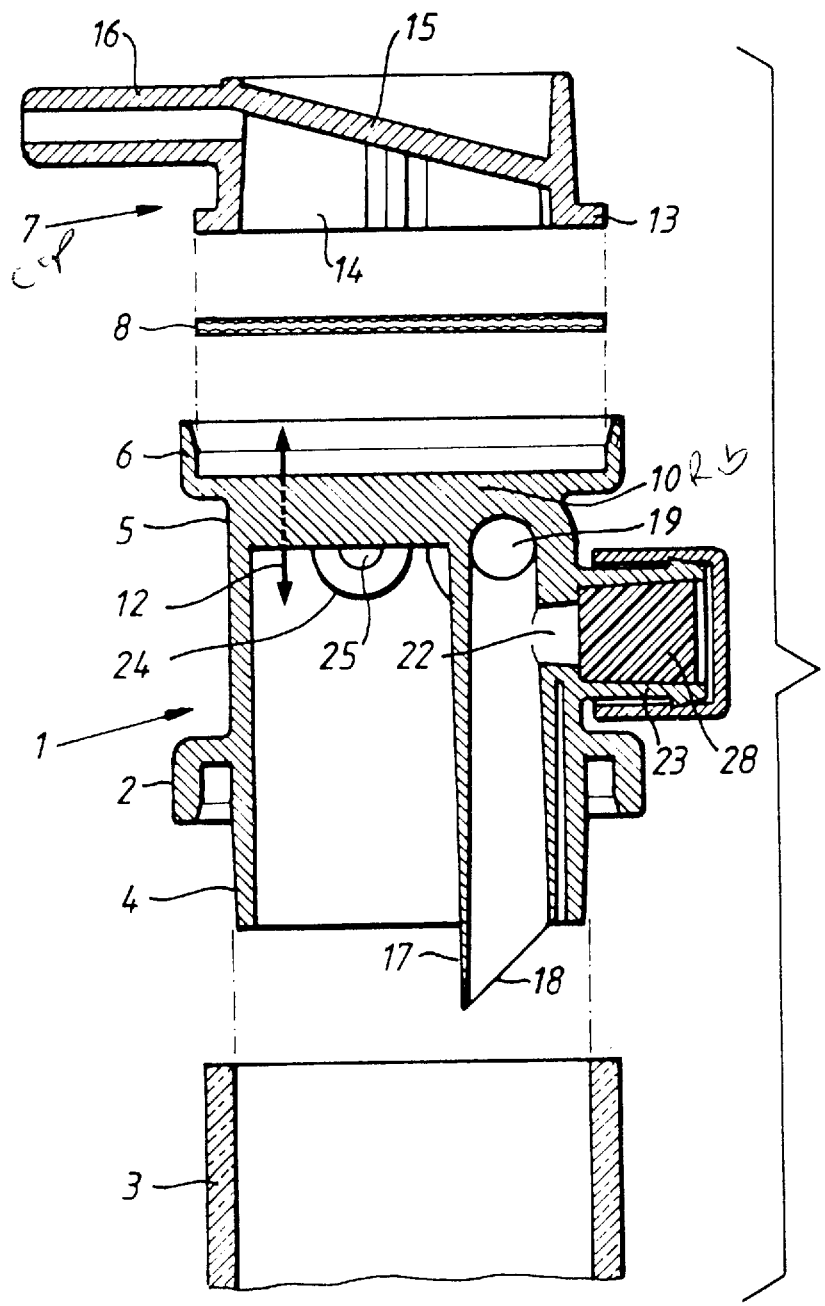
FIG. 1 is an exploded, side, cross-sectional, elevational view of a preferred embodiment of a drip chamber head according to the present invention.

A drip chamber head 1 according to the present invention is shown in FIG. 1. The head 1 is provided with a downwardly facing flange 2 which is intended to cooperate with the upper edge of a drip chamber head 3 of which only the upper portion is shown in FIG. 1.

The head 1 is substantially cylindrical and comprises a downwardly projecting lower portion 4 beneath the flange 2 and an upper portion 5 arranged above the flange 2. The upper portion 5 is provided on its upper surface with a collar 6 for cooperation and location of a cap 7. A membrane 8 is positioned in the collar 6 between the cap 7 and the upper portion 5.

Figure 2:
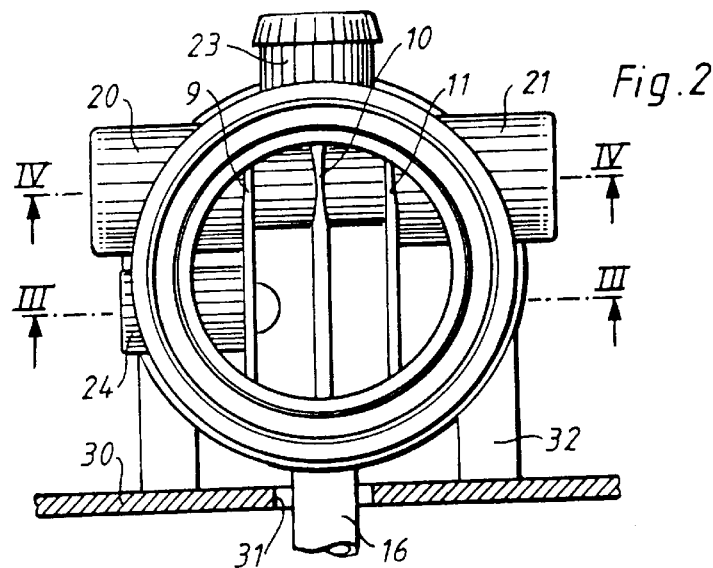
FIG. 2 is a top, plan view of the drip chamber head of the present invention with the filter cap and membrane removed, according to an alternative embodiment of the drip chamber head according to the present invention.
Figure 3:
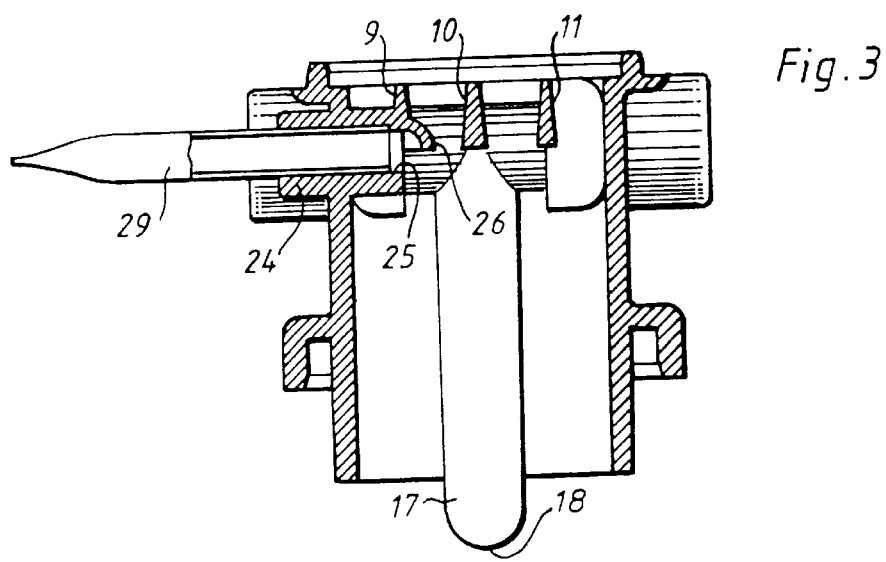
FIG. 3 is a side, elevational, cross-sectional view taken along line III—III in FIG. 2.

As is more readily apparent from the plan view according to FIG. 2 and the cross-sectional view of FIG. 3, the upper surface of the upper portion 5 is bridged by three narrow ribs 9, 10 and 11. The rib 10 is shown in FIG. 1. Accordingly, passages between the ribs 9, 10 and 11 are presented for connection between the collar 6, the upper portion 5, the lower portion 4 and the drip chamber 3. Air can thus flow past the rib 10, as indicated by the double-headed arrow 12 in FIG. 1. The ribs 9, 10 and 11 are also clearly shown in FIG. 3.

The membrane 8 is of a design known per se and consists of a hydrophobic material such as PTFE (teflon) with a pore size of approximately 0.2 $\mu$m. Since the material in the membrane is hydrophobic, air can pass through the membrane relatively unhindered, though liquid such as blood is prevented from passing through the membrane. Particles larger than about 0.2 $\mu$m, i.e. bacteria and the majority of viruses, are also unable to pass across the membrane. Thus, the membrane 8 prevents blood migrating via the drip chamber head past the membrane and further to the connection arranged in the cap 7.

The cap 7 comprises a flange 13 which is intended to cooperate with the collar 6 so that the cap is permanently retained by the collar 6. The membrane 8 is fixedly clamped between the lower horizontal surface of the collar 6 and the flange 13 of the cap 7. The membrane 8 is supported from beneath the ribs 9, 10 and 11. Further ribs 14 are arranged within the cap 7 and may be arranged in a spoke-like pattern within the cap 7. The ribs 14 extend axially from an upper surface 15 which seals the cap 7 at the top and down to the membrane 8.

The cap 7 further comprises a transversely extending connection nipple 16 which is intended for connection to a pressure sensor positioned on the front of the dialysis machine. Alternatively, the connection nipple 16 can be connected to a tube (not shown) which is connected to a pressure sensor located in proximity to the position of the drip chamber on the dialysis machine. Such a pressure sensor usually comprises a luer-connection of the male type affixed to the front of the dialysis machine. The tube from the connection nipple 16 thereby terminates with a luer-connection of the female type (not shown).

The cap 7 is attached to the collar 6 with the membrane 8 positioned therebetween and is sealingly fixed to the collar in a known manner, for example by means of ultrasonic welding or an adhesive.

The connection nipple 16 thus communicates with the interior of the head 1 and the interior of the drip chamber 3 through the passages between the ribs 14, through the membrane 8 and past the ribs 9, 10 and 11 as indicated by the arrow 12. The pressure in the upper region of the drip chamber 3 can thus be sensed by means of a pressure sensor connected to the connection nipple 16. Where appropriate, the air volume within the drip chamber 3 can be adjusted through the connection nipple 16 by means of a particular pump arranged in cooperation with the pressure sensor in the dialysis machine. In order to adjust the blood level in the drip chamber, a suitable air volume is removed or supplied. The pressure in the upper region of the drip chamber is normally a slight over-pressure relative to the atmosphere, and corresponds to the venous pressure.

The drip chamber head 1 is provided with a plurality of arrangements and connections to be able to fulfil its function. Accordingly, the head 1 is provided with a drip tube 17 extending vertically downwardly into the drip chamber 3. The drip tube 17 terminates at its lower end with a chamfered edge 18. The drops issue from the tip of the edge 18. As is apparent from FIG. 1, the drip tube 17 is arranged to one side, i.e. eccentrically within the head 1.

At its upper end, the drip tube 17 cooperates with a transverse hole 19 through which the blood is supplied to the drip tube 17 and the drip chamber 3. The hole 19 extends transversely through the head 1, as is more clearly shown in FIG. 4, and is connected to a tube connection 20 at one side of the head and to a tube connection 21 at the other side of the head. Blood is supplied to the head 1 through the connection 20 and/or connection 21 by means of a fixedly connected tube and passes through the hole 19 and is diverted downwardly into the drip tube 17.

A further transverse hole 22 is located at the upper end of the drip tube 17 perpendicular to the first hole 19. The transverse hole 22 is connected to a connection 23. A rubber plug 28 made of a material which permits sealing insertion of a needle is provided in the connection 23. The plug is held in place by a cover.

The hole 22 can be used for taking samples, whereby a syringe is inserted in the connection 23 and a blood sample removed by means of drawing out the piston of the syringe. The connection 23 and the hole 22 may equally well be used for supplying a solution or a substance such as protamine or infusion solution.

A further connection 24 is provided on the side of the head 1, as shown in FIGS. 2 and 3. The connection 24 cooperates with a hole 25 which discharges in the interior of the head 1 in connection with the upper air-filled region of the drip chamber 3. The hole 25 and the connection 24 are arranged directly beneath the membrane 8 in proximity to the rib 9, as shown in FIG. 2 and FIG. 3. By means of the connection 24 and the hole 25, a solution may be added to the drip chamber 3, such as protamine or an infusion solution. For this purpose, the hole 25 is provided with a splash flange 26 which deflects the incoming solution downwardly towards the drip chamber 3. In this manner, splashes are prevented from reaching the membrane 8. The connection 24 and the hole 25 can also be used for other purposes, for example for adjusting the blood level in the drip chamber 3 by the removal or addition of air. The connection 24 is normally connected to a tube 29 which is sealed to, or provided with, a luer-connection and blocked by a clamp. The tube is always available for the addition of an infusion solution, should the patient show signs of a crisis condition. It is possible to replace the connection 24 with a luer-connection of the female type provided with a cap which is removed when the connection is to be used.

Figure 4:
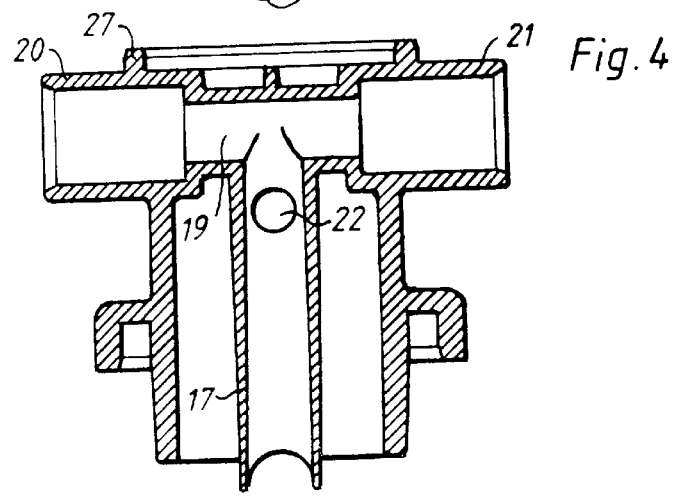
FIG. 4 is a cross-sectional view corresponding to FIG. 3, though taken along line IV—IV in FIG. 2.

As is apparent from FIGS. 2–4, an alternative fixation of the cap 7 may be employed. Thus, the collar 6 according to FIG. 1 is replaced by a ring-shaped flange 27, while the flange 13 on the cap 7 is replaced by a collar (not shown) corresponding to the collar 6.

The drip chamber 3 with the drip chamber head and cap 7 is attached to the front 30 of the dialysis machine by means of a holder 32 which is shown in FIG. 2. Thus, the blood connections 20 and 21 are horizontally positioned parallel to the front of the machine 30, which also applies for the connection 24. The sample-taking connection 23 is positioned so as to be easily accessible straight out from the front 30 of the dialysis machine. The cap 7 is positioned such that the connection nipple 16 extends through a hole 31 in the front of the dialysis machine to cooperate with a pressure sensor arranged therein (not shown). Due to the eccentric location of the drip tube 17 and the connections 20 and 21, the hole 25 and the connection 24 are permitted to be short so that no unnecessary collection of blood occurs in the hole 25. Such a collection could result in aggregation of blood and the formation of blood clots.

By integrating a blood filter 8 and a connection nipple 16 to a pressure sensor with the drip chamber head, at least one tube with associated disc filter can be eliminated from the previously used set of tubes. By arranging the connections 20, 21, and 24 horizontally and parallel to the front 30 implies that it is possible to connect tubes included in a set of tubes for an extracorporeal blood cycle in a lucid manner.

With certain forms of dialysis, such as hemodialysis, only one inlet for blood is necessary, whereby either one of the blood connections 20 and 21 can be blocked. Alternatively, the drip chamber head can be manufactured in two (or more) versions where one of the blood connections 20 or 21 is omitted.

With other forms of dialysis, such as hemofiltration, the one blood connection can be used for blood and the other for post-infusion solution. In this manner, the blood and the infusion solution are effectively mixed by means of the change in direction down the drip tube 17.

By arranging the membrane 8 in the upper end surface of the drip chamber head, a sufficiently large membrane surface is attained for integration of a membrane of standard type without substantially increasing the dimension of the drip chamber head relative to known types.

In FIG. 3, three ribs are shown for supporting the membrane, though other similar lower support constructions can be used, such as a loose metal net or ribs having other configurations.

The splash flange 26 may be further downwardly extended or replaced in its entirety by a downwardly directed tube in order to reduce the risk of splashing the membrane. Other types of membrane can be used, even hydrophillic, if such are desired.

The invention has been described above with reference to preferred embodiments of the invention. These embodiments may be modified by the skilled person in many ways and such modifications obvious to a skilled person are intended to be comprised within the scope of the invention. The various described components can be combined in other ways than those which are shown in the drawings. The invention is limited only by the appended claims.

I claim:

1. A drip chamber head for attachment to a drip chamber, said drip chamber head comprising a vertically arranged body portion having an upper portion and a lower portion, first connection means for connecting said body portion to a supply of blood and a drip member disposed within said body portion and including an upper portion and a depending lower portion, said upper portion of said drip member being in communication with said first connecting means whereby said blood may be supplied to said drip chamber through said first connecting means and said drip member, thereby providing said blood at an adjustable level within said drip chamber with an air filled region thereabove, second connecting means disposed at said upper portion of said body portion communicating with said air filled region of said drip chamber, a cap disposed at said upper portion of said body portion for closing off said lower body portion, and an air permeable filter disposed at said upper portion of said body portion between said cap and said lower body portion above said adjustable level of said blood within said drip chamber whereby the air pressure within said air filled region of said drip chamber can be sensed through said second connecting means.

2. The drip chamber head of claim 9 wherein said lower portion and said upper portion are substantially cylindrical about an axis thereby defining an effective cylindrical area, and wherein said air permeable filter has an effective cylindrical area substantially the same as said effective cylindrical area, said air permeable filter being arranged substantially perpendicularly to said axis of said cylinder.

3. The drip chamber head of claim 1 wherein said cap includes said second connecting means.

4. The drip chamber head of claim 3 wherein said second connecting means comprises a transversely extending nipple.

5. The drip chamber head of claim 3 including rib means extending transversely across said upper portion of said lower body portion thereby forming passage means between said second connecting means and said air filled region of said drip chamber, said rib means providing support for said filter.

6. The drip chamber head of claim 5 wherein said rib means comprises a plurality of rib members.

7. The drip chamber head of claim 5 wherein said rib means comprises first rib means, and including second rib means disposed in said cap above said filter for providing further support for said filter.

8. The drip chamber head of claim 1 wherein said filter comprises a membrane.

9. The drip chamber head of claim 8 wherein said membrane has a pore size of about 0.2 $\mu$m.

10. The drip chamber head of claim 1 including rib means extending transversely across said upper portion of said body portion thereby forming air passage means between said second connecting means and said air filled region of said drip chamber.

11. The drip chamber head of claim 10 wherein said rib means comprise a plurality of rib members.

* * * * *

UNITED STATES PATENT AND TRADEMARK OFFICE
CERTIFICATE OF CORRECTION

PATENT NO. : 5,851,202
DATED : December 22, 1998
INVENTOR(S) : Carlsson

It is certified that error appears in the above-identified patent and that said Letters Patent is hereby corrected as shown below:

Column 6, line 16, "9" should read --1--.

Signed and Sealed this

Eighteenth Day of May, 1999

Attest:

Q. TODD DICKINSON

*Attesting Officer*    *Acting Commissioner of Patents and Trademarks*